(12) United States Patent
Choi et al.

(10) Patent No.: US 10,718,759 B2
(45) Date of Patent: Jul. 21, 2020

(54) TRANSPARENT IMMUNOASSAY APPARATUS AND METHOD

(71) Applicant: ELECTRONICS AND TELECOMMUNICATIONS RESEARCH INSTITUTE, Daejeon (KR)

(72) Inventors: Yo-Han Choi, Daejeon (KR); Ki-Bong Song, Daejeon (KR)

(73) Assignee: ELECTRONICS AND TELECOMMUNICATIONS RESEARCH INSTITUTE, Daejeon (KR)

(*) Notice: Subject to any disclaimer, the term of this patent is extended or adjusted under 35 U.S.C. 154(b) by 369 days.

(21) Appl. No.: 15/614,472

(22) Filed: Jun. 5, 2017

(65) Prior Publication Data

US 2018/0100852 A1 Apr. 12, 2018

(30) Foreign Application Priority Data

Oct. 12, 2016 (KR) .................. 10-2016-0131995

(51) Int. Cl.
*G01N 33/558* (2006.01)
*G01N 33/53* (2006.01)
(Continued)

(52) U.S. Cl.
CPC ............ *G01N 33/53* (2013.01); *B01L 3/5023* (2013.01); *G01N 21/645* (2013.01); *G01N 21/6428* (2013.01); *G01N 21/7703* (2013.01); *G01N 21/8483* (2013.01); *G01N 33/558* (2013.01); *B01L 2300/0636* (2013.01); *B01L 2300/0825* (2013.01); *B01L 2400/0406* (2013.01); *G01N 1/00* (2013.01); *G01N 35/00* (2013.01); *G01N 2021/7786* (2013.01)

(58) Field of Classification Search
CPC ...................................................... G01N 33/558
See application file for complete search history.

(56) References Cited

U.S. PATENT DOCUMENTS 5,712,170 A * 1/1998 Kouvonen ........... G01N 33/558
422/504
5,965,458 A 10/1999 Kouvonen et al.
(Continued)

FOREIGN PATENT DOCUMENTS

JP 1996-505224 A 6/1996
KR 1020100065538 A 6/2010
(Continued)

*Primary Examiner* — Christopher L Chin

(57) ABSTRACT

Disclosed herein are a transparent immunoassay apparatus and method. The transparent immunoassay apparatus includes a sample pad configured to allow a liquid specimen to be dropped thereonto, a first porous pipe configured to move the dropped specimen in a lateral flow manner, an immunobinding reaction unit configured to generate a detectable signal from binding of a previously applied reactant and the specimen between transparent upper and lower plates of the immunobinding reaction unit, a second porous pipe configured to move the specimen, having passed through the immunobinding reaction unit, in a lateral flow manner, and an absorption pad configured to absorb the specimen transferred from the second porous pipe.

20 Claims, 5 Drawing Sheets

(51) Int. Cl.
  *G01N 21/84*  (2006.01)
  *B01L 3/00*  (2006.01)
  *G01N 21/64*  (2006.01)
  *G01N 21/77*  (2006.01)
  *G01N 1/00*  (2006.01)
  *G01N 35/00*  (2006.01)

(56) References Cited

U.S. PATENT DOCUMENTS

| | | | |
|---|---|---|---|
| 6,537,828 B1 * | 3/2003 | Nakaya | G01N 33/558 |
| | | | 422/504 |
| 2010/0141280 A1 | 6/2010 | Yang et al. | |
| 2010/0144020 A1 | 6/2010 | Kim et al. | |
| 2011/0237452 A1 | 9/2011 | Park et al. | |
| 2012/0162653 A1 | 6/2012 | Lee et al. | |

FOREIGN PATENT DOCUMENTS

| | | |
|---|---|---|
| KR | 10-2011-0027013 A | 3/2011 |
| KR | 10-1211593 B1 | 12/2012 |
| KR | 10-2013-0113072 A | 10/2013 |
| KR | 10-2015-0020804 A | 2/2015 |

* cited by examiner

TRANSPARENT IMMUNOASSAY APPARATUS AND METHOD

CROSS REFERENCE TO RELATED APPLICATION

This application claims the benefit of Korean Patent Application No. 10-2016-0131995, filed Oct. 12, 2016, which is hereby incorporated by reference in its entirety into this application.

BACKGROUND OF THE INVENTION

1. Technical Field

The present invention relates generally to an apparatus for detecting a specific antigen or antibody contained in a liquid specimen and, more particularly, to a transparent immunoassay apparatus for reading a signal generated by antigen-antibody binding from a light-transmissive (transparent) region.

2. Description of the Related Art

Various immunoassay techniques have been used to identify the presence of a specific antigen or antibody contained in a liquid specimen derived from a living body, such as blood, spit, mucus, or urine. Enzyme-Linked Immunosorbent Assay (ELISA) is a method for linking a specimen to an antibody and measuring the amount of antibody based on the depth of a color. A test that uses the principles of ELISA has very high sensitivity, and may be performed on a variety of multiple samples. However, since ELISA involves a complicated test procedure, it may be performed only by an expert who has been technically trained to a certain level or more.

However, a rapid kit, which is a rapid reaction test kit using lateral flow, generally has sensitivity slightly lower than that of ELISA. However, such a rapid kit can be easily used by laypeople. Recently, rapid kits have come to be widely utilized in the provision of biological information over a wide range and the determination of whether a user has been infected with a disease, such as the diagnosis of pregnancy and the diagnosis of diabetes and blood pressure. Such a rapid kit is generally arranged such that fibrous filters derived from an organic material are stacked in a plastic housing. In this case, biochemical components, such as an antibody, a buffer solution, and the labeled substances that are used for the rapid kit, may differ depending on the detection target. Further, in immunological tests using a rapid kit, the presence or absence of a detection target is observed with the naked eye.

The rapid kit chiefly adopts gold nanoparticles as labeled substances and uses the fact that, when gold nanoparticles gather in a specific region, they can be observed with the naked eye. In this case, a conventional rapid kit performs an immunobinding reaction on an opaque porous medium. Due thereto, quantitative analysis based on the amount of transmitted light is impossible, and thus to date tests have chiefly been dependent only on visual examination.

Therefore, in parallel with existing visual examination, the development of technology that is capable of analyzing precise and quantitative results of a rapid kit is required. In connection with this, Korean Patent No. 10-1211593 (Date of Publication: Jan. 7, 2013) discloses a technology related to "Diagnostic kit for H9 type avian influenza virus using rapid immunochromatography and the method for diagnosing H9 type avian influenza by using the same."

SUMMARY OF THE INVENTION

Accordingly, the present invention has been made keeping in mind the above problems occurring in the prior art, and an object of the present invention is to enable the result of an immunobinding reaction to be read by the naked eye.

Another object of the present invention is to measure the amount of transmitted light corresponding to the result of an immunobinding reaction and quantitatively analyze the result of the immunobinding reaction.

In accordance with an aspect of the present invention to accomplish the above objects, there is provided a transparent immunoassay apparatus, including a sample pad configured to allow a liquid specimen to be dropped thereonto, a first porous pipe configured to move the dropped specimen in a lateral flow manner, an immunobinding reaction unit configured to generate a detectable signal from binding of a previously applied reactant and the specimen between transparent upper and lower plates of the immunobinding reaction unit, a second porous pipe configured to move the specimen, having passed through the immunobinding reaction unit, in a lateral flow manner, and an absorption pad configured to absorb the specimen transferred from the second porous pipe.

The reactant to react with the specimen may be applied to a first surface of at least one of the upper and lower plates.

An amount of transmitted light in the signal generated from binding of a detection target contained in the specimen and the reactant may be read as a result of examination corresponding to the specimen.

The immunobinding reaction unit may read the generated signal using at least one of a light source unit provided on a first side of the immunobinding reaction unit and a light detection unit provided on a second side of the immunobinding reaction unit.

The sample pad may be configured such that an antibody corresponding to the detection target contained in the specimen is applied to the sample pad, and the detection target contained in the specimen may move in the lateral flow manner, with the detection target being bound to the antibody applied to the sample pad.

The previously applied reactant may be at least one of a normal antibody, an antibody to which gold nanoparticles are attached, and an antibody to which an enzyme is attached.

When the previously applied reactant is the antibody to which the enzyme is attached, a substrate corresponding to the enzyme injected into the first porous pipe may generate the detectable signal by causing an enzyme reaction with the antibody to which the enzyme is attached.

The immunobinding reaction unit may be configured such that at least one of a hydrophilic film and a hydrophobic film is formed on at least one of the upper and lower plates.

The immunobinding reaction unit may be configured such that a blocking film for preventing adsorption of materials other than a material in which the reactant and the specimen are bound together is formed on at least one of the upper and lower plates.

In accordance with another aspect of the present invention to accomplish the above objects, there is provided an immunoassay method performed by a transparent immunoassay apparatus, including receiving a liquid specimen, moving the specimen in a lateral flow manner through a first porous pipe, bringing a previously applied reactant into contact with the specimen between transparent upper and lower plates, detecting a signal generated by the contact of the reactant with the specimen, moving the specimen in a lateral flow manner through a second porous pipe, and absorbing the specimen transferred from the second porous pipe.

The reactant may react with the specimen and may be applied to a first surface of at least one of the upper and lower plates.

Detecting the signal may be configured to read a result of examination corresponding to the specimen based on an amount of transmitted light in the signal generated from binding of a detection target contained in the specimen with the reactant.

Detecting the signal may be configured to read the generated signal using at least one of a light source unit provided on a first side of the transparent immunoassay apparatus and a light detection unit provided on a second side of the transparent immunoassay apparatus.

Receiving the specimen may be configured to receive the specimen through a sample pad to which an antibody corresponding to the detection target contained in the specimen is applied, and moving the specimen through the first porous pipe may be configured to move the specimen in which the detection target is bound to the antibody applied to the sample pad.

The previously applied reactant may be at least one of a normal antibody, an antibody to which gold nanoparticles are attached, and an antibody to which an enzyme is attached.

Detecting the signal may be configured to, when the previously applied reactant is the antibody to which the enzyme is attached, detect the signal generated when a substrate corresponding to the enzyme injected into the first porous pipe causes an enzyme reaction with the antibody to which the enzyme is attached.

At least one of a hydrophilic film and a hydrophobic film may be formed on at least one of the upper and lower plates.

A blocking film may be formed on at least one of the upper and lower plates, the blocking film being configured to prevent adsorption of materials other than a material in which the reactant and the specimen are bound together.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Figure 1:
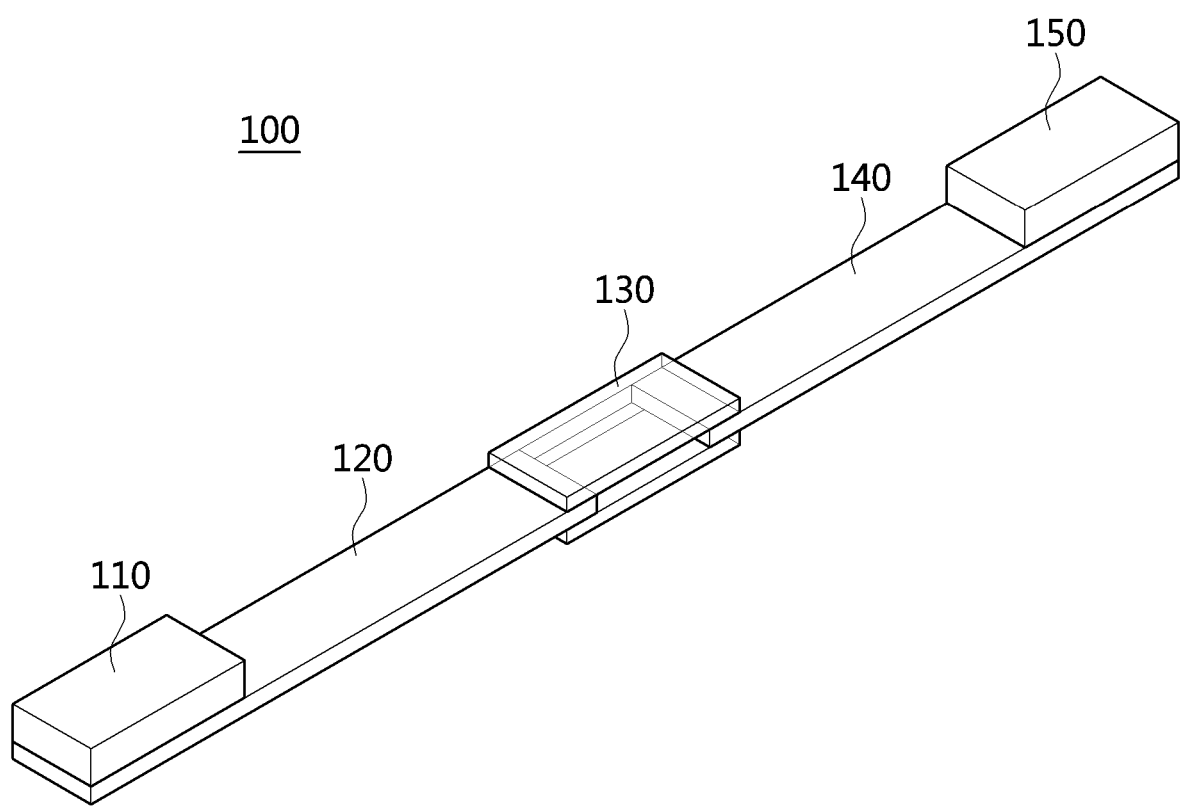
FIG. 1 is a perspective view illustrating the configuration of a transparent immunoassay apparatus according to an embodiment of the present invention.

The present invention may be variously changed and may have various embodiments, and specific embodiments will be described in detail below with reference to the attached drawings.

However, it should be understood that those embodiments are not intended to limit the present invention to specific disclosure forms and they include all changes, equivalents or modifications included in the spirit and scope of the present invention.

The terms used in the present specification are merely used to describe specific embodiments and are not intended to limit the present invention. A singular expression includes a plural expression unless a description to the contrary is specifically pointed out in context. In the present specification, it should be understood that the terms such as "include" or "have" are merely intended to indicate that features, numbers, steps, operations, components, parts, or combinations thereof are present, and are not intended to exclude a possibility that one or more other features, numbers, steps, operations, components, parts, or combinations thereof will be present or added.

Unless differently defined, all terms used here including technical or scientific terms have the same meanings as the terms generally understood by those skilled in the art to which the present invention pertains. The terms identical to those defined in generally used dictionaries should be interpreted as having meanings identical to contextual meanings of the related art, and are not interpreted as being ideal or excessively formal meanings unless they are definitely defined in the present specification.

Embodiments of the present invention will be described in detail with reference to the accompanying drawings. In the following description of the present invention, the same reference numerals are used to designate the same or similar elements throughout the drawings and repeated descriptions of the same components will be omitted.

FIG. 1 is a perspective view illustrating the configuration of a transparent immunoassay apparatus according to an embodiment of the present invention.

As shown in FIG. 1, a transparent immunoassay apparatus 100 includes a sample pad 110, a first porous pipe 120, an immunobinding reaction unit 130, a second porous pipe 140, and an absorption pad 150.

The transparent immunoassay apparatus 100 may be implemented in the form of a rapid kit that uses a lateral flow and may follow the usage method for a typical rapid kit, but the immunobinding reaction unit 130 in which visual sensing is performed is manufactured to be transparent.

Further, the transparent immunoassay apparatus 100 according to an embodiment of the present invention uses, as a basic mechanism, a structure in which light incident on the immunobinding reaction unit 130 is absorbed or blocked by any one of reaction products of an immunoconjugate generated via binding of a specimen and an reactant, gold nanoparticles conjugated to the immunoconjugate, and an enzyme conjugated to the immunoconjugate, and then only a part of the incident light is sensed from the surface opposite the surface on which the light is incident.

As shown in FIG. 1, the transparent immunoassay apparatus 100 may have a shape in which the sample pad 110, the first porous pipe 120, the immunobinding reaction unit 130, the second porous pipe 140, and the absorption pad 150 are sequentially arranged, and may be arranged such that first (or second) ends thereof overlap other components (or modules).

Further, a liquid specimen is injected into the sample pad 110, and the injected specimen permeates through the first porous pipe 120 and then moves to the immunobinding reaction unit 130. In the immunobinding reaction unit 130, a signal is generated due to a reaction between the specimen and the reactant, and the specimen is absorbed into the absorption pad 150 through the second porous pipe 140 after the reaction has occurred.

Furthermore, the sample pad 110, the first porous pipe 120, the immunobinding reaction unit 130, the second porous pipe 140, and the absorption pad 150 may be enclosed in a housing functioning as a physical support, and then the transparent immunoassay apparatus 100 may be implemented. Here, as a material for the housing, polystyrene, polypropylene, polycarbonate, cyclic olefin copolymer, or the like may be used.

In addition, the sample pad 110, the first porous pipe 120, the upper/lower plates of the immunobinding reaction unit 130, the second porous pipe 140, and the absorption pad 150 may be implemented to be attached to each other via a chemical adhesive, a physical adhesive, pressurizing, housing, etc.

Hereinafter, individual components of the transparent immunoassay apparatus 100 will be described in greater detail.

First, a liquid specimen is dropped onto the sample pad 110. Here, the liquid specimen may be any one of blood, spit, mucus, and urine. Also, the liquid specimen dropped onto the sample pad 110 moves to the first porous pipe 120 through capillary force or the like.

Further, an antibody corresponding to a detection target contained in the specimen may be applied to the sample pad 110. When the antibody corresponding to the detection target is applied to the sample pad 110, the detection target contained in the specimen may be bound to the antibody applied to the sample pad 110, and may move in a lateral flow manner. Furthermore, a material such as a surfactant, salts, a buffer, or a blocking material may be applied to the sample pad 110.

Furthermore, the sample pad 110 may be arranged such that all or part of thereof overlaps the first porous pipe 120, and may be disposed on the top of the first end of the first porous pipe 120, as shown in FIG. 1.

The sample pad 110 may be made of a material corresponding to any one of paper, an organic polymer, and a glass fiber. Also, the sample pad 110 may be a simple reticular tissue or may be a glass fiber filter, a cellulose filter, or a polyester filter. The material of the sample pad 110 is not limited to this example, and the specification of the sample pad 110 is not limited to that shown in FIG. 1.

Further, the first porous pipe 120 moves the specimen transferred from the sample pad 110 in a lateral flow manner. When the antibody corresponding to the detection target is applied to the sample pad 110, a form in which the detection target and the antibody are bound together may move through the first porous pipe 120.

A substrate corresponding to the enzyme may be injected into the first porous pipe 120. When a reactant is applied to the immunobinding reaction unit 130 and the applied reactant is an antibody to which the enzyme is attached, the substrate corresponding to the enzyme may be injected into the first porous pipe 120.

The first porous pipe 120 may be arranged such that the first end thereof overlaps the sample pad 110 and the second end thereof overlaps the immunobinding reaction unit 130.

Further, the first porous pipe 120 may be made of a material corresponding to any one of paper, an organic polymer, and a glass fiber, and especially a nitrocellulose, polyvinylidene fluoride, nylon, or polyethersulfone. The material of the first porous pipe 120 is not limited to this example, and the specification of the first porous pipe 120 is not limited to that illustrated in FIG. 1.

Next, the immunobinding reaction unit 130 is provided with transparent upper and lower plates, and the immunobinding reaction unit 130 is a region in which the previously applied reactant and the specimen are bound together to generate a detectable signal.

The immunobinding reaction unit of a conventional rapid kit was made of an opaque material. When light is emitted onto a signal generated from the opaque material, dispersion occurs while the emitted light is reflected from a signal region, and thus only part of the incident light is sensed. Therefore, the conventional immunobinding reaction unit made of the opaque material has very low sensitivity. As a result, it has been possible to measure absorbance based on incidence and reflection only when the concentration of a detection target is very high, as in the case of creatinine or albumin contained in urine.

On the other hand, the immunobinding reaction unit 130 of the transparent immunoassay apparatus 100 according to an embodiment of the present invention is configured such that a signal depending on the binding of the reactant and the specimen is generated between the transparent upper and lower plates. By way of the signal, light absorption (extinction) occurring in a light transmission procedure may be measured, and quantitative analysis of a reaction result is possible.

The upper and lower plates of the immunobinding reaction unit 130 may be each made of a material corresponding to any one of a transparent organic polymer, glass, and a transparent inorganic mineral substance, and may be made of the same material or different materials.

In this case, the transparent organic polymer used to form the upper and lower plates may be, but is not limited to, any one selected from the group consisting of polystyrene, polyethylene, polypropylene, polycarbonate, polyvinylidene fluoride, a variant thereof, cyclic olefin copolymer, and polydimethylsiloxane.

The immunobinding reaction unit 130 may be formed by joining the transparent upper and lower plates to each other, where the upper and lower plates may be joined to each other using a chemical adhesive, tape, or the like. Further, the immunobinding reaction unit 130 may also be formed via physical joining based on an external housing, and such a joining method is not limited to any specific method.

The reactant previously applied to the immunobinding reaction unit 130 may be applied to one surface of at least one of the upper and lower plates of the immunobinding reaction unit 130. Also, the reactant previously applied to the immunobinding reaction unit 130 may be bound to the specimen, and thus a detectable signal is generated.

Further, the region of the immunobinding reaction unit 130, other than the region to which the reactant is applied, is treated to be blocked, and thus a blocking film may be formed. Furthermore, at least one of a hydrophilic film and a hydrophobic film for controlling hydrophilicity and hydrophobicity, respectively, may be formed on one surface of at least one of the upper and lower plates of the immunobinding reaction unit 130.

Meanwhile, a light source unit may be provided on a first side of the immunobinding reaction unit 130 and a light detection unit (photodetection unit) may be provided on a second side of the immunobinding reaction unit 130. In this case, the light source unit and the light detection unit may be provided at symmetric positions with respect to the immunobinding reaction unit 130. For example, when the light source unit is located on the top of the immunobinding reaction unit 130, the light detection unit may be located on the bottom of the immunobinding reaction unit 130.

In the light source unit, a specific light source may be installed outside the transparent immunoassay apparatus 100 so as to emit an amount of light having a designated wavelength onto the immunobinding reaction unit 130, wherein the type of light source is not limited to a specific type.

In this way, the transparent immunoassay apparatus 100 according to the embodiment of the present invention may be provided with the light source unit and the light detection unit, thus quantitatively analyzing signals resulting from an immunobinding reaction. Conventional immunoassay devices caused a user to read signals resulting from an immunobinding reaction with the naked eye of the user. However, the transparent immunoassay apparatus 100 according to the embodiment of the present invention may quantitatively read signals using the light source unit and the light detection unit.

Further, at least one of the hydrophilic film and the hydrophobic film may be formed on at least one of the upper and lower plates of the immunobinding reaction unit 130. Furthermore, a blocking film for preventing the adsorption of materials other than a material in which the reactant and the specimen are bound together may be formed on at least one of the upper and lower plates of the immunobinding reaction unit 130.

The immunobinding reaction unit 130 may be arranged such that the first end thereof overlaps the second end of the first porous pipe 120 and such that the second end thereof overlaps the first end of the second porous pipe 140. In particular, as shown in FIG. 1, the first and second porous pipes 120 and 140 may be arranged such that the second end of the first porous pipe 120 and the first end of the second porous pipe 140 overlap the immunobinding reaction unit 130 between the upper and lower plates of the immunobinding reaction unit 130.

The second porous pipe 140 moves the specimen, which has passed through the immunobinding reaction unit 130, in a lateral flow manner.

The second porous pipe 140 may be made of a material corresponding to any one of paper, an organic polymer, and a glass fiber, and may be made of, for example, a material selected from the group consisting of nitrocellulose, polyvinylidene fluoride, nylon, and polyethersulfone. The material of the second porous pipe 140 is not limited to these examples, and the specification of the second porous pipe 140 is not limited to that shown in FIG. 1. Further, the material and specification of the second porous pipe 140 may be identical to or different from those of the first porous pipe 120.

The second porous pipe 140 may be arranged such that the first end thereof overlaps the immunobinding reaction unit 130 and the second end thereof overlaps the absorption pad 150.

The absorption pad 150 finally absorbs the specimen transferred from the second porous pipe 140. The absorption pad 150 absorbs excess specimen, or absorbs the specimen with which a reaction has been terminated.

A material such as a surfactant, salts, a buffer, or a blocking material may be previously applied to the absorption pad 150. Further, the absorption pad 150 may be a cellulose filter.

The absorption pad 150 may be made of a material corresponding to any one of paper, an organic polymer, and a glass fiber. The material of the absorption pad 150 is not limited to these examples, and the specification of the absorption pad 150 is not limited to that shown in FIG. 1. Further, the material and specification of the absorption pad 150 may be identical to or different from those of the sample pad 110.

Further, the absorption pad 150 may be arranged to overlap the second end of the second porous pipe 140. In particular, the absorption pad 150 may be disposed on the top of the second end of the second porous pipe 140 so that all of the absorption pad 150 overlaps the second porous pipe 140.

Physical specifications of the transparent immunoassay apparatus 100, such as the materials, widths, lengths, and thicknesses of the sample pad 110, the first porous pipe 120, the second porous pipe 140, and the absorption pad 150, may be selected in consideration of the properties of the specimen and the detection target, and are not limited to specific specifications in the present invention.

Figure 2:
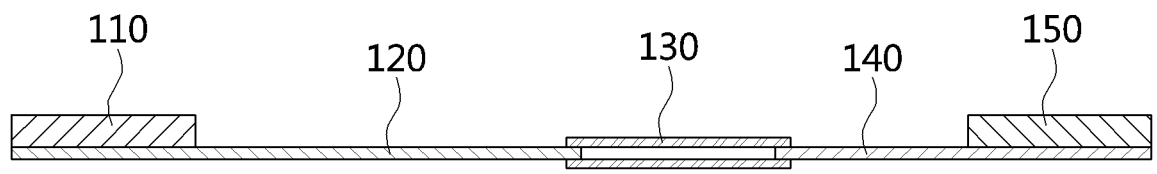
FIG. 2 is a sectional view illustrating the section of a transparent immunoassay apparatus according to an embodiment of the present invention.

FIG. 2 is a sectional view illustrating the section of the transparent immunoassay apparatus according to an embodiment of the present invention.

As shown in FIG. 2, the transparent immunoassay apparatus 100 may be implemented such that the sample pad 110, the first porous pipe 120, the immunobinding reaction unit 130, the second porous pipe 140, and the absorption pad 150 are sequentially arranged.

In particular, as shown in FIG. 2, the sample pad 110 may be disposed on the top of the first end of the first porous pipe 120, and part or all of the sample pad 110 may overlap the first porous pipe 120. Further, the first end of the first porous pipe 120 may overlap the sample pad 110, and the second end of the first porous pipe 120 may overlap the immunobinding reaction unit 130.

The first porous pipe 120 may be partially interposed between the upper and lower plates of the immunobinding reaction unit 130, and thus part of the first porous pipe 120 and part of the immunobinding reaction unit 130 may overlap each other.

Further, the first end of the second porous pipe 140 may overlap the immunobinding reaction unit 130, the second end of the second porous pipe 140 may overlap the absorption pad 150, and the second porous pipe 140 may be partially interposed between the upper and lower plates of the immunobinding reaction unit 130.

Furthermore, the second end of the second porous pipe 140 may overlap part or all of the absorption pad 150. As shown in FIG. 2, the absorption pad 150 may be implemented so as to be disposed on the top of the second porous pipe 140.

Figure 3:
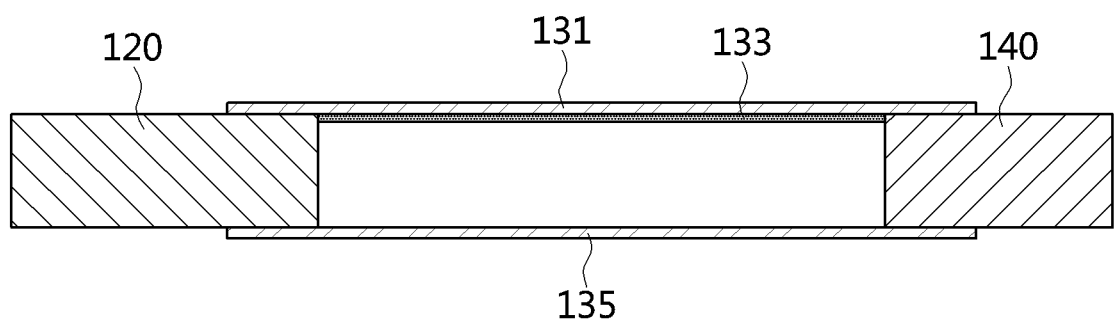
FIG. 3 is a sectional view illustrating the section of the immunobinding reaction unit of the transparent immunoassay apparatus according to an embodiment of the present invention.

FIG. 3 is a sectional view illustrating the section of the immunobinding reaction unit of the transparent immunoassay apparatus according to an embodiment of the present invention. As shown in FIG. 3, the immunobinding reaction unit 130 of the transparent immunoassay apparatus 100 is interposed between the first porous pipe 120 and the second porous pipe 140. Further, the first end of the immunobinding reaction unit 130 may overlap the first porous pipe 120 and the second end of the immunobinding reaction unit 130 may overlap the second porous pipe 140.

The immunobinding reaction unit 130 may include a transparent upper plate 131 and a transparent lower plate 135. Each of the upper plate 131 and the lower plate 135 may be made of any one selected from the group consisting of a transparent organic polymer, glass, and a transparent inorganic mineral substance. Furthermore, the upper plate 131 and the lower plate 135 may be made of the same material or different materials.

In particular, each of the upper plate 131 and the lower plate 135 may be implemented in the form of a membrane made of an organic polymer, an inorganic polymer, glass, or a silicon compound. Here, the silicon compound may be silicon nitride or silicon oxide.

The organic polymer used to form the immunobinding reaction unit 130 may be, but is not limited to, any one selected from the group consisting of polystyrene, polyethylene, polypropylene, polycarbonate, polyvinylidene fluoride, a variant thereof, cyclic olefin copolymer, and polydimethylsiloxane.

Further, a reactant 133 that reacts with the specimen may be applied to one surface of at least one of the upper plate 131 and the lower plate 135 of the immunobinding reaction unit 130. In FIG. 3, although the reactant 133 is illustrated as being applied to one surface of the upper plate 131, the present invention is not limited thereto, and the reactant 133 may be applied to one surface of the lower plate 135 or to one surface of each of the upper plate 131 and the lower plate 135.

The reactant 133 may be an antibody corresponding to a detection target, i.e. to the antigen desired to be detected, and the kind, concentration, and the amount of antibody may differ depending on the detection target. Here, an amount of antibody sufficient to collect all of the detection target may be applied to the immunobinding reaction unit 130.

For example, the antibody may be contained in a medium such as a saline solution at a concentration of 0.1 mg/ml to 1 mg/ml, and may then be applied to the immunobinding reaction unit 130. A solution containing the antibody may be dried to such an extent that a portion of the medium remains in order to allow the activity of the antibody to be maintained. Further, depending on the materials and properties of the upper plate 131 and the lower plate 135 of the immunobinding reaction unit 130, the amount of antibody, i.e. of the reactant 133, may be controlled.

The reactant 133 may be applied to the immunobinding reaction unit 130 using any of various methods such as spotting, stamping, and soft lithography, and the method of applying the reactant to the immunobinding reaction unit 130 is not limited to these examples.

Further, the reactant 133 may be attached to the detection target of the specimen via electrostatic adsorption, which is a noncovalent-bond attachment method, and may also be attached using a specific response that uses protein A, protein G, protein A/G, or the like. Furthermore, the reactant 133 may be attached to the detection target via a covalent bond, such as the formation of a disulfide bridge, but the method of attaching the reactant 133, i.e. the antibody, is not limited to these examples.

A hydrophilic film and a hydrophobic film for controlling hydrophilicity and hydrophobicity, respectively, may be formed on one surface of at least one of the upper plate 131 and the lower plate 135 of the immunobinding reaction unit 130. The hydrophilic film and the hydrophobic film may be formed using chemical, biochemical or physical surface treatment. Here, each film may be implemented using a method based on ozone, polylysine, or fine etching, and a film-forming method is not limited to these examples.

Further, one surface of at least one of the upper plate 131 and the lower plate 135 of the immunobinding reaction unit 130 may be treated to be blocked, and then a blocking film may be formed thereon. Here, the blocking film may be formed in a region of the upper plate 131 and the lower plate 135 other than the region to which the reactant 133 is applied.

The blocking film denotes a film for preventing the adsorption of materials other than a material in which the reactant and the specimen are bound together. In this case, the blocking film may be made of proteins, such as albumin or casein, or peptides which are broken down proteins.

Further, blocking treatment may be performed as a procedure of treating the inner surface of at least one of the upper plate 131 and the lower plate 135 of the immunobinding reaction unit 130 with a blocking solution such as an albumin or casein solution at a concentration of about 1% for one minute or longer and cleansing the inner surface with a cleansing solution such as a phosphate-buffered saline (PBS) so as to eliminate an excess blocking solution. Here, the kind of blocking solution and the kind of cleansing solution are not limited to specific examples.

Hereinafter, the movement of a specimen dropped onto the transparent immunoassay apparatus according to an embodiment of the present invention will be described in greater detail with reference to FIGS. 4 to 7.

FIGS. 4 to 7 are diagrams for explaining the movement of a specimen dropped onto the transparent immunoassay apparatus according to an embodiment of the present invention.

Figure 4:
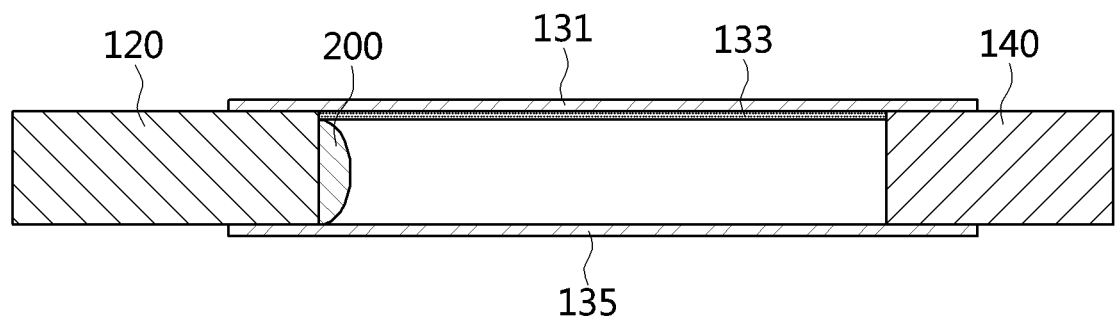
FIGS. 4 to 7 are diagrams for explaining the movement of a specimen dropped onto the transparent immunoassay apparatus according to an embodiment of the present invention.
Figure 5:
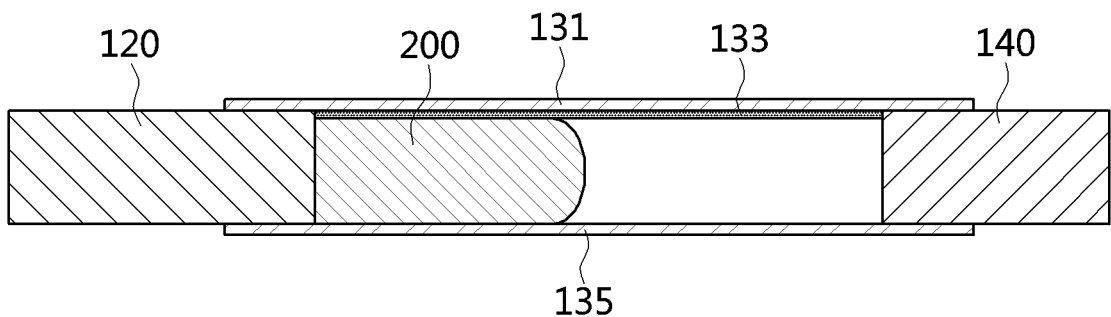
Figure 6:
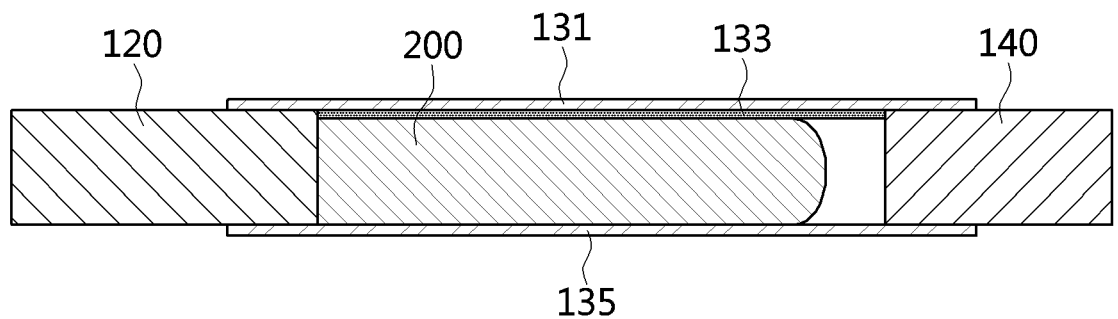
Figure 7:
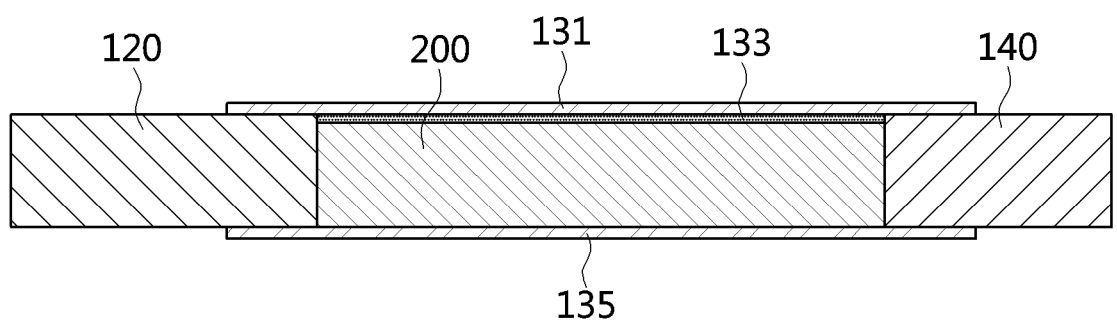

As shown in FIG. 4, a specimen 200 transferred through the first porous pipe 120 in a lateral flow manner moves between the transparent upper and lower plates 131 and 135. The liquid specimen 200, which has reached the end portion of the first porous pipe 120, permeates and moves through the second porous pipe 140 while filling a gap between the upper plate 131 and the lower plate 135.

Further, as shown in FIGS. 4 to 7, as the specimen 200 moves, the reactant 133 applied to one surface of the upper plate 131 is transferred to the second porous pipe 140, with the reactant 133 being attached to a detection target contained in the specimen 200. Further, the liquid specimen 200, which has reached the second porous pipe 140, continues to laterally flow and then reaches the absorption pad 150.

The speed at which the liquid specimen 200 moves in the transparent immunoassay apparatus 100 may be controlled by providing a hydrophilic film on at least one of the upper plate 131 and the lower plate 135.

Hereinafter, an immunoassay method performed by the transparent immunoassay apparatus according to an embodiment of the present invention will be described in greater detail with reference to FIG. 8.

Figure 8:
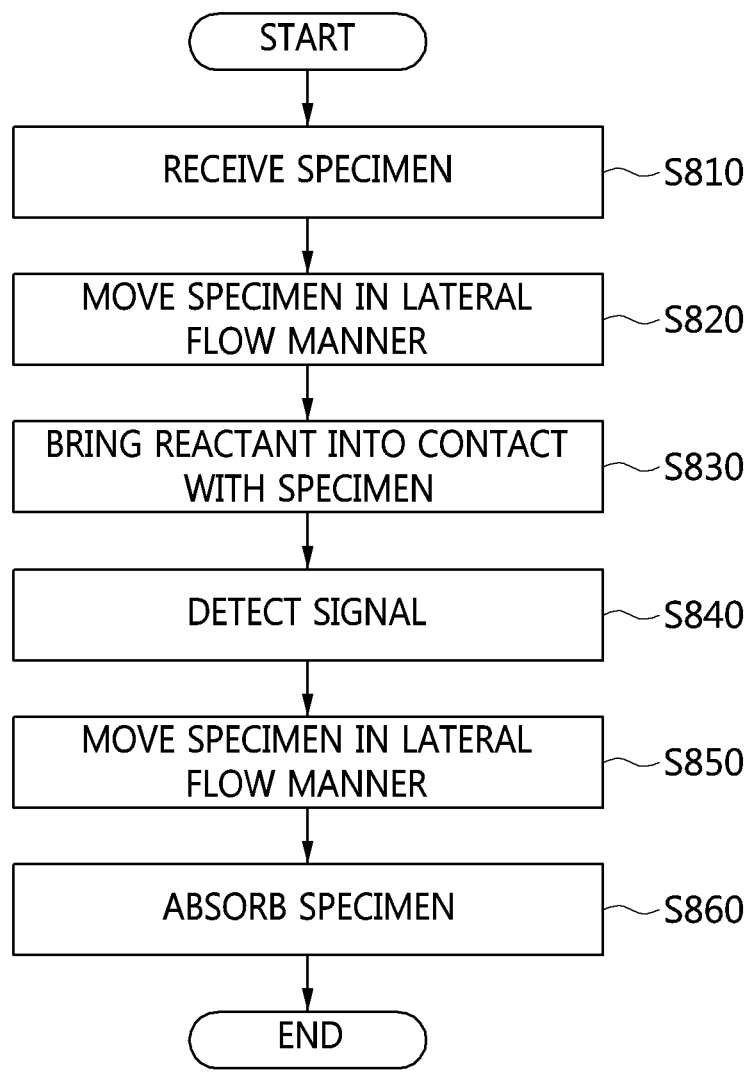
FIG. 8 is a flowchart for explaining an immunoassay method performed by the transparent immunoassay apparatus according to an embodiment of the present invention.

FIG. 8 is a flowchart for explaining an immunoassay method performed by the transparent immunoassay apparatus according to an embodiment of the present invention.

First, the sample pad of the transparent immunoassay apparatus 100 receives a specimen at step S810.

The sample pad of the transparent immunoassay apparatus 100 receives a liquid specimen, such as blood, spit, mucus, or urine. An antibody to be attached to a specific material contained in the specimen may be previously applied to the sample pad. When the antibody is applied to the sample pad, the antibody previously applied to the sample pad is attached to the specific material in the specimen and then moves to the first porous pipe.

Here, the antibody previously applied to the sample pad may be at least one of a normal antibody, an antibody to which gold nanoparticles are attached, and an antibody to which an enzyme is attached, but the type of antibody used to detect an individual specific material is not limited thereto.

Next, the first porous pipe of the transparent immunoassay apparatus 100 moves the specimen in a lateral flow manner at step S820.

The specimen received by the sample pad moves to the immunobinding reaction unit through the first porous pipe. In this case, the specimen may move in the direction of fluid flow occurring due to a capillary phenomenon.

Then, the immunobinding reaction unit of the transparent immunoassay apparatus 100 brings a reactant into contact with the specimen at step S830.

When the specimen is transferred to the immunobinding reaction unit through the first porous pipe, the liquid specimen moves to the second porous pipe while filling the gap between the upper and lower plates of the immunobinding reaction unit.

A detection target contained in the specimen is attached to the immunobinding reaction unit due to the reactant applied to the immunobinding reaction unit. Here, the reactant may be any one of a normal antibody, an antibody to which gold nanoparticles are attached, and an antibody to which an enzyme is attached.

Further, when the antibody is previously applied to the sample pad, the detection target to which any one of the normal antibody, a gold nanoparticle, and an enzyme is attached may be attached to the immunobinding reaction unit.

Next, the transparent immunoassay apparatus 100 detects a signal resulting from a reaction between the reactant and the specimen at step S840.

When an antibody to which gold nanoparticles are attached is used as the reactant, the transparent immunoassay apparatus 100 emits light from a position corresponding to any one of the upper and lower plates of the immunobinding reaction unit while receiving light at the side opposite the side from which light is emitted, thus enabling the amount of transmitted light to be measured.

Further, when an antibody to which an enzyme is attached is used as the reactant, the transparent immunoassay apparatus 100 may additionally inject an enzyme substrate into the first porous pipe. Furthermore, the material generated as the result of the reaction with the enzyme may be a material having a specific wavelength, and may be a blocking material for blocking light.

In order to detect a signal corresponding to the result of the reaction with the enzyme, the transparent immunoassay apparatus 100 may emit light from a position corresponding to any one of the upper and lower plates of the immunobinding reaction unit, and may receive light at the opposite position thereof, thus enabling the signal to be detected. In this case, light may be emitted using a light source having a specific wavelength, and light sources having different wavelengths may be used depending on the type of substrate.

At step S840, the signal may be detected using the transparent immunoassay apparatus 100 by performing an existing visual examination or by performing a visual examination and measuring the amount of transmitted light in parallel. Here, when an optical device for measuring the amount of transmitted light is used, a result that is more precise and quantitative may be detected.

A conventional rapid kit performs an immunobinding reaction on an opaque porous medium. Due thereto, quantitative analysis based on the amount of transmitted light is impossible, and thus examination has chiefly been dependent on visual examination. An optical measurement-based quantitative method that has chiefly been utilized in urine examination uses the reflection of light, and is possible only when the amount of material that is desired to be detected is large.

However, the transparent immunoassay apparatus 100 according to an embodiment of the present invention may detect an antigen-antibody complex, or a substrate reactant resulting from the antigen-antibody complex, based on the amount of transmitted light, by utilizing the transparent immunobinding reaction unit.

Next, the second porous pipe of the transparent immunoassay apparatus 100 moves the specimen in a lateral flow manner at step S850, and the absorption pad absorbs the specimen at step S860.

Here, the extent and speed of flow of the specimen may be controlled using the materials, thicknesses, widths, and lengths of the second porous pipe and the absorption pad of the transparent immunoassay apparatus 100.

The transparent immunoassay apparatus 100 according to the embodiment of the present invention may be applied to technology for producing a chemical reaction in a transparent region and detecting the result of the chemical reaction based on the amount of transmitted light using an optical measuring device. Further, the transparent immunoassay apparatus 100 may also be applied to technology for detecting creatinine contained in urine using picric acid.

In accordance with the present invention, the result of an immunobinding reaction may be easily read by the naked eye.

Further, in accordance with the present invention, the amount of transmitted light corresponding to the result of an immunobinding reaction may be measured, and then the result of the immunobinding reaction may be quantitatively analyzed.

As described above, in the transparent immunoassay apparatus and method according to the present invention, the configurations and schemes in the above-described embodiments are not limitedly applied, and some or all of the above embodiments can be selectively combined and configured so that various modifications are possible.

What is claimed is:

1. A transparent immunoassay apparatus, comprising:
    a sample pad to receive a liquid specimen having a detection target;
    a first porous pipe coupled to the sample pad and receive the specimen;
    an immunobinding reaction unit coupled to the first porous pipe, the immunobinding reaction unit having first and second transparent plates and a reactant, the immunobinding reaction unit being capable of generating a signal from binding of the reactant and the detection target in the specimen;
    a second porous pipe coupled to the immunobinding reaction unit; and
    an absorption pad coupled to the second porous pipe to absorb the specimen from the second porous pipe.

2. The transparent immunoassay apparatus of claim 1, wherein the reactant is applied to the first transparent plate.

3. The transparent immunoassay apparatus of claim 2, wherein the first transparent plate is an upper plate and the second transparent plate is a lower plate, and
    wherein an amount of transmitted light in the signal generated from binding of the detection target contained in the specimen and the reactant is read as a result of examination corresponding to the specimen.

4. The transparent immunoassay apparatus of claim 3, wherein the generated signal is read using at least one of a light source unit provided on a first side of the immunobinding reaction unit and a light detection unit provided on a second side of the immunobinding reaction unit.

5. The transparent immunoassay apparatus of claim 3, wherein:
the sample pad is configured such that an antibody corresponding to the detection target contained in the specimen is applied to the sample pad, and
the detection target contained in the specimen flows laterally with the detection target being bound to the antibody applied to the sample pad.

6. The transparent immunoassay apparatus of claim 5, wherein the reactant is an antibody to which gold nanoparticles or an enzyme is not attached, an antibody to which gold nanoparticles are attached, an antibody to which an enzyme is attached, or a combination thereof.

7. The transparent immunoassay apparatus of claim 6, wherein, when the reactant is the antibody to which the enzyme is attached, a substrate corresponding to the enzyme injected into the first porous pipe generates the signal by causing an enzyme reaction with the antibody to which the enzyme is attached.

8. The transparent immunoassay apparatus of claim 2, wherein the immunobinding reaction unit includes a film formed on the first transparent plate, the film being hydrophilic or hydrophobic.

9. The transparent immunoassay apparatus of claim 2, wherein the immunobinding reaction unit includes a blocking film provided on the first transparent plate, the blocking film preventing adsorption of materials other than a material in which the reactant and the specimen are bound together.

10. The transparent immunoassay apparatus of claim 8, wherein the film is a hydrophilic film.

11. The transparent immunoassay apparatus of claim 8, wherein the film is a hydrophobic film.

12. The transparent immunoassay apparatus of claim 8, wherein the reactant is formed on the first transparent plate.

13. The transparent immunoassay apparatus of claim 8, wherein the reactant is formed on the second transparent plate.

14. The immunoassay apparatus of claim 8, wherein the first transparent plate is a lower plate and the second transparent plate is an upper plate.

15. An immunoassay apparatus, comprising:
a first pad to receive a liquid specimen having a detection target; and
a first channel having a first end and a second end, the first end of the first channel being coupled to the pad;
an immunobinding reaction unit coupled to the second end of the first channel and having first and second transparent plates and a reactant, the immunobinding reaction unit being capable of generating a signal from binding of the reactant and the detection target in the specimen.

16. The immunoassay apparatus of claim 15, further comprising:
a second channel having a first end and a second end, the first end of the second channel being coupled to the immunobinding reaction unit; and
a second pad coupled to second end of the second channel.

17. The immunoassay apparatus of claim 16, wherein the reactant is provided on the first transparent plate of the immunobinding reaction unit, and
wherein the first and second channels are porous pipes.

18. The immunoassay apparatus of claim 17, further comprising a first film provided over the second transparent plate.

19. The immunoassay apparatus of claim 18, wherein the first film is blocking film, a hydrophilic film, or a hydrophobic film.

20. The immunoassay apparatus of claim 18, further comprising a second film provided over the second transparent plate.

* * * * *